United States Patent [19]

Bailey et al.

[11] Patent Number: Plant 7,395

[45] Date of Patent: Dec. 11, 1990

[54] CHRYSANTHEMUM PLANT NAMED YELLOW FRESCO

[75] Inventors: George A. Bailey, Great Yarmouth; Kieth G. Lintott, Chichester, both of England

[73] Assignee: Framptons Nurseries Ltd., West Sussex, England

[21] Appl. No.: 164,462

[22] Filed: Mar. 4, 1988

[51] Int. Cl.[5] ..... A01H 5/00

[52] U.S. Cl. ..... Plt./78

[58] Field of Search ..... Plt./78

*Primary Examiner*—Robert E. Bagwill

*Attorney, Agent, or Firm*—Brisebois & Kruger

[57] ABSTRACT

A new variety of *Chrysanthemum morifolium* Bailey of the yellow spray type, known as "Yellow Fresco" and characterized by a long flowering season, fast response, moderate growth, resistance to petal damping, and non-susceptibility to tip scorch/loss.

1 Drawing Sheet

This invention relates to a new and distinct variety of *Chrysanthemum morifolium* bailey (spray type) known as "Yellow Fresco".

My new variety "Yellow Fresco" is a yellow sport from the variety White Fresco. White Fresco resulted from an extensive breeding program to produce improved varieties for year round Chrysanthemum production, particularly for winter production. White Fresco is a white sport found in the variety Pink Fresco, which orginiated from a cross between the variety Rosechip and the variety Artic, the former being the seed parent and the latter being the pollen parent.

The variety Pink Fresco resulted from an extensive breeding program to produce improved varieties for year round Chrysanthemum production, particularly for winter production.

I discovered the mutation known as "Yellow Fresco" in 1984, in a nursery in Martham, Great Yarmouth, Norfolk, England.

Yellow Fresco has the following improved characteristics over the variety Improved Yellow Hurricane, the most similar year round spray type grown in Great Britain.

1. Yellow Fresco has a longer flowering season, earlier and later, than Improved Yellow Hurricane.
2. Yellow Fresco is not susceptible to tip scorch.
3. Yellow Fresco is much less prone to petal damping than Improved Yellow Hurricane.
4. The response of Yellow Fresco is faster than Improved Yelow Hurricane at most times of the year.
5. Less vigorous than Improved Yellow Hurricane, Yellow Fresco does not stretch to produce long pedicels requiring growth regulator treatment.
6. The flower size of Yellow Fresco is slightly smaller than Improved Yellow Hurricane.

Asexual production of this new variety "Yellow Fresco" as performed in Sussex, England, by rooting vegetative shoots shows that the above characteristics are fixed and come true to type through succeeding generations.

The accompanying drawing shows a typical flower of my new variety depicted in color as nearly true as it is reasonably possible to make the same in a color illustration of this type.

The following is a detailed description of the new variety "Yellow Fresco" with color terminology in accordance with The Royal Horticultural Society Colour Chart, (R.H.S.).

Genus: Chrysanthemum.

Species: Morifolium Bailey.

Type: Spray.

Class: Decorative.

Breeding: A cultivated sport or mutation of "White Fresco" which was a sport found in the variety "Pink Fresco" which was a cross between the variety "Rosechip" and the variety Artic, the former being the seed parent and the latter being the pollen parent.

Propagation: Holds its distinguishing characteristics through succeeding propations by rooting vegetative shoots.

Flowers: As grown and observed in Sussex, England, 6 to 12 flowers are borne on pedicels, after removal of the main apical bud.

Bloom:

*Size.*—Diameter of 6.0 cm. to 8.5 cm. when fully open.

*Form.*—Decorative, slightly reflexing.

*Petalage.*—250 to 275 Ray petals. 4 to 6 Disc Petals.

*Form.*—Decorative, slightly reflexing.

*Petals.*—Medium, short, overlapping, pointed of medium texture.

*Pedicels.*—Thick and strong, 10 cm. to 15 cm. long.

*Color of open bloom.*—Inner face of fully expanded petal: R.H.S. 13B. Outer face of fully expanded petal: R.H.S. 13B. Inner face of young petal: R.H.S. 13A. Outer face of young petal: R.H.S. 13A.

Response group: 10 weeks.

Temperature tolerance: 13° C. – 18° C. (56° F. – 65° F.) at night.

Plant: Strong upright habit of growth, medium vigor.

Foliage: Good quality with average internode length of 2.5 cm; Medium size and medium texture; color R.H.S. 133A.

Stem: Upright, medium thickness and strong. Color R.H.S. 139A at flowering.

Water uptake: Good.

I claim:

1. A new and distinct variety of *Chrysanthemum morifolium* bailey of the yellow spray type substantially as herein shown and described characterized particularly as to novelty by a long flowering season, fast response, moderate growth, resistance to petal damping, and non-susceptibility to tip scorch/loss.

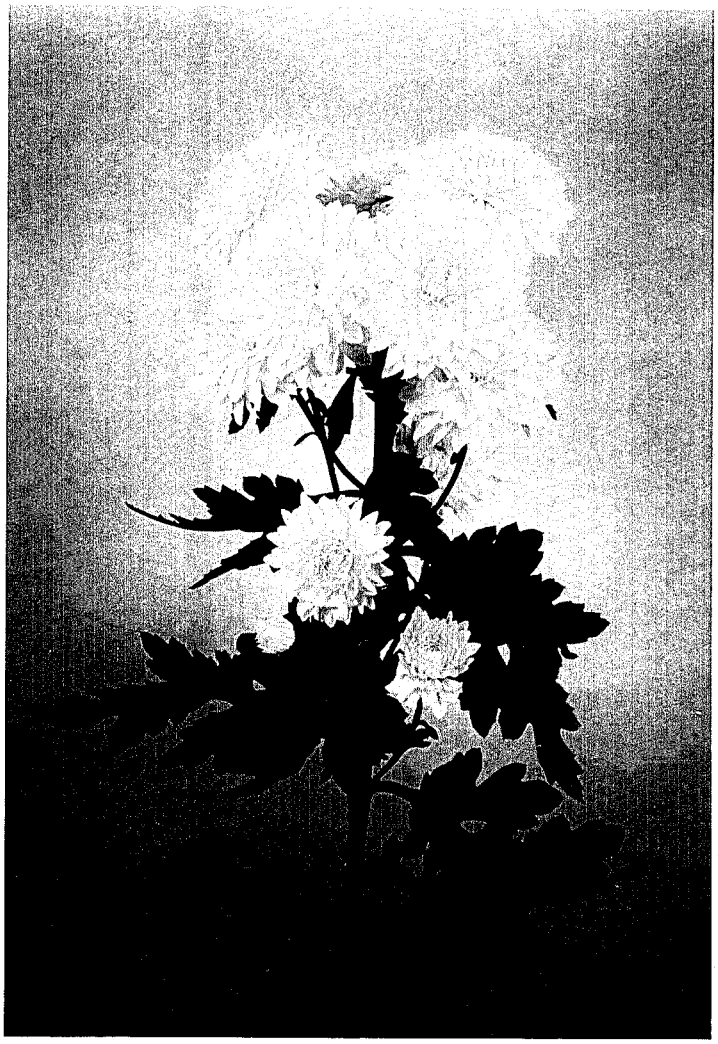

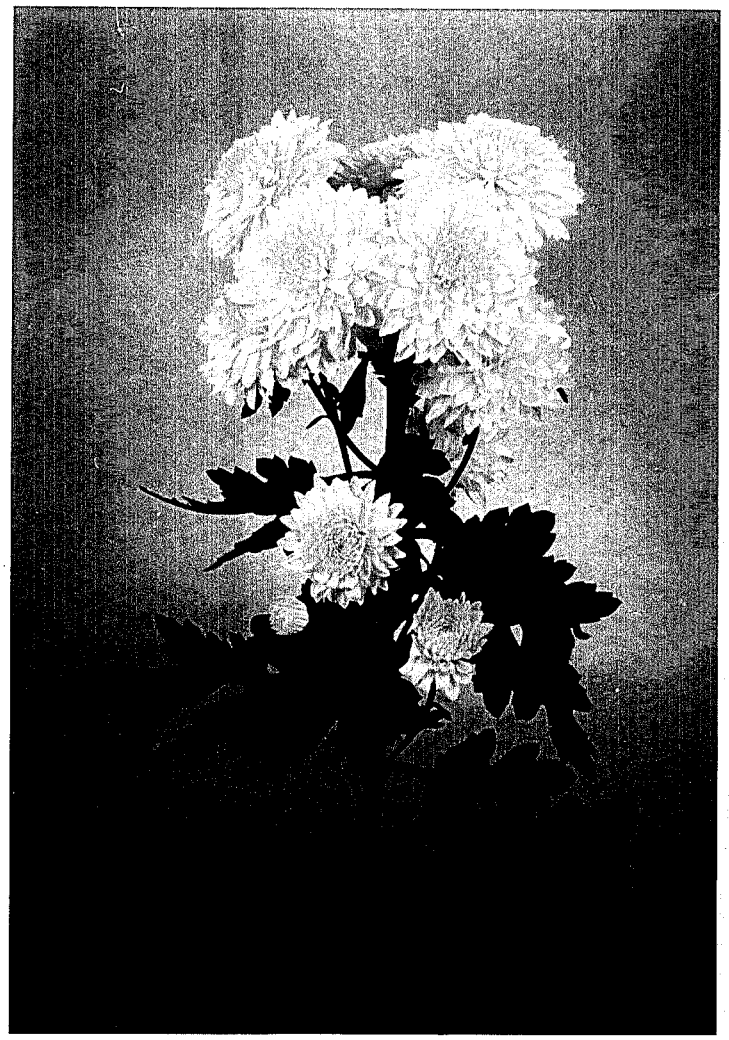

* * * * *